United States Patent
Rothe

(10) Patent No.: US 11,662,321 B2
(45) Date of Patent: *May 30, 2023

(54) SCATTER CORRECTION FOR COMPUTED TOMOGRAPHY IMAGING

(71) Applicant: Baker Hughes Oilfield Operations LLC, Houston, TX (US)

(72) Inventor: Nils Rothe, Hürth (DE)

(73) Assignee: Baker Hughes Oilfield Operations LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/492,525

(22) Filed: Oct. 1, 2021

(65) Prior Publication Data

US 2022/0113266 A1    Apr. 14, 2022

Related U.S. Application Data

(60) Provisional application No. 63/090,144, filed on Oct. 9, 2020.

(51) Int. Cl.
*A61B 6/00* (2006.01)
*G01N 23/046* (2018.01)
*G06T 5/00* (2006.01)
*G06T 5/50* (2006.01)

(52) U.S. Cl.
CPC ......... *G01N 23/046* (2013.01); *A61B 6/5282* (2013.01); *G06T 5/001* (2013.01); *G06T 5/50* (2013.01); *G01N 2223/401* (2013.01); *G06T 2207/10081* (2013.01); *G06T 2207/20084* (2013.01)

(58) Field of Classification Search
None
See application file for complete search history.

(56) References Cited

U.S. PATENT DOCUMENTS

| 6,618,466 | B1 | 9/2003 | Ning | |
| 9,804,106 | B2 | 10/2017 | Rothe | |
| 2016/0258885 | A1* | 9/2016 | Rothe | G01N 23/046 |
| 2021/0059625 | A1* | 3/2021 | Bai | G06N 3/08 |

FOREIGN PATENT DOCUMENTS

| WO | 2016141956 A1 | 9/2016 |
| WO | 2017048548 A1 | 3/2017 |

OTHER PUBLICATIONS

John et al "Neural network scatter correction technique for digital radiography", SPIE, Medical Imaging, 1990, p. 462-471. (Year: 1990).*

* cited by examiner

*Primary Examiner* — David P Porta
*Assistant Examiner* — Mamadou Faye
(74) *Attorney, Agent, or Firm* — Mintz Levin Cohn Ferris Glovsky and Popeo, PC

(57) ABSTRACT

Systems and methods for scatter correction of x-ray images are provided. A scatter image of an object can be corrected using partial-scatter free images acquired using an aperture plate. The plate is positioned between an object and a radiation detector and includes apertures in a grid. The original x-rays pass through the apertures and scattered x-rays can be blocked by the aperture plate. The aperture plate can be moved to different positions, allowing partial scatter-free images to be acquired at each position of the aperture plate. A full scatter-free image can be generated by combining partial scatter-free images. The scatter and scatter-free images can be further used to train scatter correction models.

12 Claims, 17 Drawing Sheets

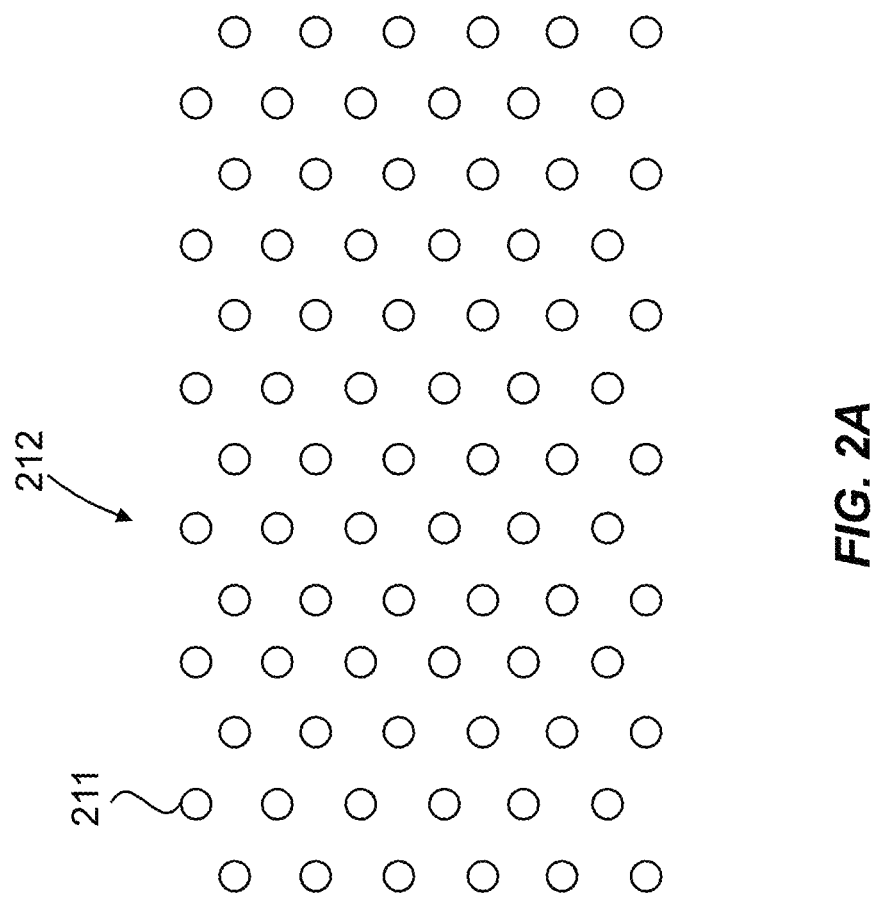

SCATTER CORRECTION FOR COMPUTED TOMOGRAPHY IMAGING

CROSS-REFERENCE TO RELATED APPLICATIONS

This application claims the benefit of U.S. Provisional Patent Application No. 63/090,144, filed on Oct. 9, 2020, and entitled "Scatter Correction For Computed Tomography Imaging," the entirety of which is incorporated by reference.

BACKGROUND

Inspection of objects is commonly performed in manufacturing and repair industries. Various types of inspection systems can be used in industrial inspection processes, such as computed tomography (CT), coordinate measuring machines (CMM), laser-based profilometry, light gauge, infrared and others. For example, these inspection systems can be used to measure dimensions or to identify defects in manufactured parts (e.g., turbine blades).

Each of these inspection systems has its advantages and disadvantages. Modalities such as CMM and laser-based profilometry can be used to measure external surfaces with high accuracy but they cannot measure internal features unless the object is cut open. To date, CT is the most versatile of the measurement/inspection systems for revealing both the internal and external structures of industrial parts in a non-destructive manner. Because of their ability to provide internal as well as external measurements, CT based techniques may facilitate processes such as reverse engineering, rapid prototyping, casting simulation and validation, tire development, first article inspection, ceramic porosity inspection, process validation, parts qualification and defect detection, among others.

SUMMARY

However, CT based techniques may also have certain limitations, which may deter their widespread use. For example, volumetric computerized tomography (VCT) imaging for industrial applications (e.g., imaging of metallic parts) can provide unsatisfactory images having image artifacts due to radiation-matter interaction based artifacts, scanner based artifacts, reconstruction techniques based artifacts, and so forth. The radiation-matter interaction based artifacts may further include beam hardening artifacts and artifacts due to x-ray scatter radiations. Scatter radiation is a strong function of the imaging parameters such as the object under imaging, beam spectrum used, geometrical distances, and the surrounding medium. In general, scatter radiation in the projection images can be undesirable, as it can reduce the contrast of the projection images, produce degradation of or blurs sharp features of the object in the generated volume images, and reduce the accuracy of metrology applications and the detectability of smaller features.

Accordingly, various techniques have been developed to estimate scatter in order to reduce or eliminate it from CT images. In general, due to various dependencies in the imaging parameters, an accurate estimation of the scatter signal content in projection imaging can be challenging. Physics-based models are often used for predicting scatter content in x-ray images, however they are time consuming and predict only scatter arising out of the object under scanning, provided the material properties are known.

There exist different techniques for scatter measurement and scatter correction in acquired projection images. For example, one popular scatter measurement technique employs a beam stopper located between the radiation source and the object being scanned in a VCT system to measure the scatter at a corresponding location. However, most currently known techniques primarily address the object scatter and involve time-consuming computer simulations.

As manufacturing tolerances become tighter, there is a corresponding increase in the demands for metrology techniques for maintaining the tolerances. The need for quality and performance testing has become an integral part of the production or manufacturing process. Thus, in order to improve CT inspection accuracy and efficiency, more effective methods are needed for removing scatter radiation related artifacts.

Embodiments of the present disclosure provide improved systems and methods for scatter correction. A scatter image of an object can be corrected using additional images acquired with a scatter rejecting aperture plate. The scatter rejecting aperture plate can include a plurality of apertures positioned on a grid. In use, the aperture plate is positioned between an object being imaged and a detector. When collimated x-rays are directed from an x-ray source to the object, the original x-rays can pass through the apertures, while a significant fraction of scattered x-rays can be blocked by the aperture plate. The aperture plate can also be configured to move between different positions. Thus, partial scatter-free images can be acquired at each position of the aperture plate, referred to herein as partial scatter-free images. A scatter-free image (ground truth) can be obtained by combining the partial scatter-free images. The number of positions and acquired partial scatter-free images can be varied, depending on the geometry of the aperture plate. In general, the number of positions can be sufficient such that the apertures cover the entire area of scattered image which is to be scatter corrected.

The above-discussed embodiment relies upon the use of an aperture plate having discrete holes, also referred to as a beam hole, to acquire partial scatter-free images. In alternative embodiments, slit collimators or beam stops can be employed in lieu of the aperture plate to acquire partial scatter free images. Similar to the aperture plate approach, the slit collimator or beam stop can be positioned between the radiation source and the detector and moved. Each partial scatter-free image can be acquired at a different position of the slit collimator or beam stop and the partial scatter-free images can be combined to form the scatter-free image.

The scatter-free image acquired by use of any of the aperture plate, slit collimator, or beam stops, can be further used to facilitate scatter correction. In one aspect, the scatter-free image can be used as a reference for training a neural network to determine an algorithm for scatter correction. In another aspect, the scatter-free image can be used to determine the point spread function (PSF) for a scatter deconvolution algorithm.

In further embodiments, partial scatter free images or scatter-free images can be used to adjust an already trained neural network or to adjust parameters for a known PSF for convolutional-based scatter correction.

In an embodiment, a method for scatter correction of an image of an object is provided. The method can include acquiring, by a radiation detector of an imaging system, data representing at least one scatter image of an object based upon detection of radiation that is transmitted through an imaging volume of the object. The method can further include placing an aperture plate between the object and the radiation detector at a first position. The aperture plate can include a plurality of apertures configured to inhibit scattered radiation from detection by the radiation detector. The method can also include acquiring, by the radiation detector, data representing at least one first partial scatter-free image based upon detection of radiation that is transmitted through the imaging volume of the object when the aperture plate is in the first position. The method can additionally include moving the aperture plate to one or more second positions, different from the first position. The apertures of the first position and one or more second positions can cover the area of the object captured within the at least one scattered image. The method can also include acquiring, by the radiation detector, data representing at least one second partial scatter-free image based upon detection of radiation that is transmitted through the imaging volume of the object when the aperture plate is in the one or more second positions. The method can further include receiving, by an analyzer including one or more processors, the at least one first and second partial scatter-free image data. The method can additionally include generating, by the analyzer, at least one scatter-free image based upon a combination of at least a portion of the at least one first partial scatter-free image data and at least a portion of the at least one second partial scatter-free image data. The method can also include updating, by the analyzer, a scatter correction model using at least a portion of the at least one scatter image and the at least one scatter-free image. The method can further include outputting, by the analyzer, the updated scatter correction model.

In another embodiment, the scatter correction model can be a neural network model including a scatter correction algorithm. The method can further include operations performed by the analyzer including updating the scatter correction model by operations including applying the scatter correction algorithm to at least a portion of the at least one scatter image to generate a scatter-corrected image, determining a deviation between the generated scatter-corrected image and the at least one scatter-free image. The operations can additionally include, when the deviation is greater than a predetermined deviation, updating the scatter correction algorithm to reduce the deviation. The operations can further include, when the deviation is less than or equal to the predetermined deviation, outputting the updated scatter correction model including the updated scatter correction algorithm.

In another embodiment, the scatter correction model can be a deconvolution including a scatter edge spread function (ESF). The scatter edge spread function can further include a point spread function (PSF) configured to correct scatter within a scatter image. The method can further include updating the scatter correction model. The scatter correction model can be updated by operations including applying the PSF to at least a portion of the at least one scatter image to generate a scatter-corrected image and determining a deviation between the scatter-corrected image and the at least one scatter-free image. The operations can further include, when the deviation is above a predetermined deviation, updating parameters of the PSF to reduce the deviation and repeating said applying and determining operations. The operations can additionally include, when the deviation is below the predetermined deviation, outputting the updated scatter correction model including the updated PSF parameters.

In another embodiment, the detected radiation can be collimated.

In another embodiment, the at least one scatter free image is not generated by interpolation of the at least one first partial scatter-free image data or the at least one second partial scatter-free image data.

In another embodiment, moving the aperture plate can include at least one of a unidirectional translation, a bidirectional translation, or a rotation.

In another embodiment, the at least one scatter image can be a scatter image set including a plurality of images.

In another embodiment, the apertures can be arranged in a two-dimensional grid.

In another embodiment, the apertures in the first position and at the least one second position can overlap one another.

In another embodiment, the apertures in the first position and the at least one second position can be spaced apart by a predetermined distance from one another.

In an embodiment, an imaging system is provided. The imaging system can include a radiation source, a moveable aperture plate, and an analyzer. The radiation source can be configured to emit radiation directed towards an object. The radiation detector can be configured to detect the emitted radiation transmitted through an imaging volume of the object. The moveable aperture plate can be positioned between the object and the radiation detector and it can further include a plurality of apertures configured to inhibit scattered radiation from detection by the radiation detector. The analyzer can include one or more processors. The analyzer can be further configured receive data representing at least one scatter image of the object based upon detection of radiation transmitted through an imaging volume of the object. The analyzer can also be configured to receive data representing at least one first partial scatter-free image of the object based upon detection of radiation that is transmitted through the imaging volume of the object when the aperture plate is in a first position. The analyzer can be additionally configured to receive data representing at least one second partial scatter-free image based upon detection of radiation that is transmitted through the imaging volume of the object when the aperture plate is in one or more second positions, different from the first position. The apertures in the first position and the one or more second positions can cover the area of the object captured within the at least one scattered image. The analyzer can also be configured to generate at least one scatter-free image based upon a combination of at least a portion of the at least one first partial scatter-free image data and at least a portion of the at least one second partial scatter-free image data. The analyzer can be further configured to train a scatter correction model using at least a portion of the at least one scatter image and the at least one scatter-free image. The analyzer can be additionally configured to output the trained scatter correction model.

In another embodiment, the scatter correction model can be a neural network model including a scatter correction algorithm. The analyzer can be further configured to train the scatter correction algorithm by applying the scatter correction algorithm to at least a portion of the at least one scatter image to generate a scatter-corrected image and determining a deviation between the generated scatter-corrected image and the at least one scatter-free image. When the deviation is greater than a predetermined deviation, the analyzer can further update the scatter correction algorithm to reduce the deviation. When the deviation is less than or equal to the predetermined deviation, the analyzer can further output the updated scatter correction algorithm.

In another embodiment, the scatter correction model can be a deconvolution including a scatter edge spread function (ESF). The scatter edge spread function can further include a point spread function (PSF) configured to correct scatter within a scatter image. The analyzer can be further configured to train the PSF by applying the PSF to at least a portion of the at least one scatter image to generate a scatter-corrected image and determining a deviation between the scatter-corrected image and the at least one scatter-free image. When the deviation is above a predetermined deviation, the analyzer can further update the parameters of the PSF to reduce the deviation and repeating said applying and determining operations. When the deviation is below the predetermined deviation, the analyzer can output the PSF parameters.

In another embodiment, the system can further include a collimator configured to collimate the emitted radiation.

In another embodiment, the analyzer is not configured to generate the at least one scatter free image by interpolation of the at least one first partial scatter-free image data or the at least one second partial scatter-free image data.

In another embodiment, the first and at least one second positions can differ by at least one of a unidirectional translation, a bidirectional translation, or a rotation.

In another embodiment, the at least one scatter image can be a scatter image set including a plurality of images.

In another embodiment, the apertures can be are arranged in a two-dimensional grid.

In another embodiment, the apertures in the first position of the aperture plate and at the least one second position of the aperture plate can overlap one another.

In another embodiment, the apertures in the first position of the aperture plate and the at least one second position of the aperture plate can be are spaced apart by a predetermined distance from one another.

In an embodiment, a method for scatter correction of an image of an object is provided. The method can include acquiring, by a radiation detector of an imaging system, data representing a plurality of scatter images of an object based upon detection of radiation that is transmitted through an imaging volume of the object. The method can also include placing an aperture plate between the object and the radiation detector. The aperture plate can include a plurality of apertures configured to inhibit scattered radiation from detection by the radiation detector. The method can further include acquiring, by the radiation detector, data representing a partial scatter-free image corresponding to each scatter image. Each partial scatter-free image can be based upon detection of radiation that is transmitted through the imaging volume of the object when the aperture plate is present. The scatter image and its corresponding partial scatter-free image can be acquired under approximately the same conditions except for the presence of the aperture plate. The method can further include receiving, by an analyzer including one or more processors, the plurality of scatter image data and corresponding partial-scatter free image data. The method can additionally include receiving, by the analyzer, a trained scatter correction model. The method can further include, by the analyzer, updating, the trained scatter correction model based upon the received plurality of scatter image data and corresponding partial-scatter free image data, to yield an updated trained scatter correction model, correcting at least one of the plurality of scatter images based upon the updated trained scatter correction model; and outputting at least one corrected scatter image.

In an embodiment, the trained scatter correction model can be a trained neural network model.

In another embodiment, updating the trained scatter correction model can include, for each pair of corresponding scatter image and partial scatter-free images, performing an interpolation between the output of the trained neural network model for the scatter image and the output of the trained neural network model for the partial scatter-free image, and generating the updated trained scatter correction model based upon the interpolation.

In another embodiment, the trained scatter correction model can include a previously determined deconvolution point spread function (PSF) estimate.

In another embodiment, updating the trained scatter correction model can include locally parametrizing the deconvolution PSF estimate using measurement points of respective pairs of corresponding scatter image and partial scatter-free images, and updating the deconvolution PSF estimate based upon the local parametrization.

In another embodiment, an imaging system is provided. The imaging system can include a radiation source, a radiation detector, and an analyzer. The radiation source can be configured to emit radiation directed towards an object. The radiation detector can be configured to detect the emitted radiation transmitted through an imaging volume of the object. The analyzer can include one or more processors. The analyzer can be further configured to receive data representing a plurality of scatter images of an object based upon detection of radiation by the radiation source that is transmitted through an imaging volume of the object. The analyzer can also be configured to receive data representing a partial scatter-free image corresponding to each scatter image. Each partial scatter-free image can be based upon detection of radiation that is transmitted through the imaging volume of the object when the aperture plate is present. The scatter image and its corresponding partial scatter-free image can be acquired under approximately the same conditions except for the presence of the aperture plate. The analyzer can further be configured to receive a trained scatter correction model and update the trained scatter correction model based upon the received plurality of scatter image data and corresponding partial-scatter free image data, to yield an updated trained scatter correction model. The analyzer can additionally be configured to correct at least one of the plurality of scatter images based upon the updated trained scatter correction model, and output at least one corrected scatter image.

In another embodiment, the trained scatter correction model can be a trained neural network model.

In another embodiment, updating the trained scatter correction model can include, by the analyzer for each pair of corresponding scatter image and partial scatter-free images, performing an interpolation between the output of the trained neural network model for the scatter image and the output of the trained neural network model for the partial scatter-free image, and generating the updated trained scatter correction model based upon the interpolation.

In another embodiment, the trained scatter correction model can include a previously determined deconvolution point spread function (PSF) estimate.

In another embodiment, updating the trained scatter correction model can include locally parametrizing the deconvolution PSF estimate using measurement points of respective pairs of corresponding scatter image and partial scatter-free images, and updating the deconvolution PSF estimate based upon the local parametrization.

In another embodiment, a method for scatter correction of an image of an object is provided. The method can include acquiring, by a radiation detector of an imaging system, data representing a plurality of scatter images of an object based upon detection of radiation that is transmitted through an imaging volume of the object. The method can further include placing an aperture plate between the object and the radiation detector. The aperture plate can include a plurality of apertures configured to inhibit scattered radiation from detection by the radiation detector. The method can additionally include acquiring, by the radiation detector, data representing a single partial scatter-free image. The single partial scatter-free image can be based upon detection of radiation that is transmitted through the imaging volume of the object when the aperture plate is present. The method can additionally include receiving, by an analyzer including one or more processors, the plurality of scatter image data and the single partial-scatter free image data. The method can also include receiving, by the analyzer, a trained scatter correction model. The method can further include updating, by the analyzer, the trained scatter correction model based upon the received plurality of scatter image data and the single partial-scatter free image data, to yield an updated trained scatter correction model. The method can additionally include correcting, by the analyzer, at least one of the plurality of scatter images based upon the updated trained scatter correction model and outputting, by the analyzer, at least one corrected scatter image.

In another embodiment, the trained scatter correction model can be a trained neural network model.

In another embodiment, updating the trained scatter correction model can include, for each image pair including a scatter image of the plurality of scatter images and the single partial scatter-free image, performing an interpolation between the output of the trained neural network model for the scatter image and the output of the trained neural network model for the single partial scatter-free image, and generating the updated trained scatter correction model based upon the interpolation.

In another embodiment, the trained scatter correction model can include a previously determined deconvolution point spread function (PSF) estimate.

In another embodiment, updating the trained scatter correction model can include locally parametrizing the deconvolution PSF estimate using measurement points of respective image pairs including a scatter image of the plurality of scatter images and the single partial scatter-free image, and updating the deconvolution PSF estimate based upon the local parametrization.

In another embodiment, an imaging system is provided and can include a radiation source, a radiation detector, and an analyzer. The radiation source can be configured to emit radiation directed towards an object. The radiation detector can be configured to detect the emitted radiation transmitted through an imaging volume of the object. The analyzer can include one or more processors. The analyzer can be also configured to receive data representing a plurality of scatter images of an object based upon detection of radiation by the radiation source that is transmitted through an imaging volume of the object. The analyzer can be further configured to receive data representing a single partial scatter-free image. The single partial scatter-free image can be based upon detection of radiation that is transmitted through the imaging volume of the object when the aperture plate is present. The analyzer can additionally be configured to receive a trained scatter correction model, update the trained scatter correction model based upon the received plurality of scatter image data and the single partial-scatter free image data, to yield an updated trained scatter correction model, correct at least one of the plurality of scatter images based upon the updated trained scatter correction model, and output at least one corrected scatter image.

In another embodiment, the trained scatter correction model can be a trained neural network model.

In another embodiment, updating the trained scatter correction model can include, for each image pair including a scatter image of the plurality of scatter images and the single partial scatter-free image, performing an interpolation between the output of the trained neural network model for the scatter image and the output of the trained neural network model for the single partial scatter-free image, and generating the updated trained scatter correction model based upon the interpolation.

In another embodiment, the trained scatter correction model can include a previously determined deconvolution point spread function (PSF) estimate.

In another embodiment, updating the trained scatter correction model can include locally parametrizing the deconvolution PSF estimate using measurement points of respective image pairs including a scatter image of the plurality of scatter images and the single partial scatter-free image, and updating the deconvolution PSF estimate based upon the local parametrization.

DESCRIPTION OF DRAWINGS

These and other features will be more readily understood from the following detailed description taken in conjunction with the accompanying drawings, in which:

FIG. 2A is a schematic diagram illustrating positions of apertures of an aperture plate when the aperture plate is located at a first position;

Figure 1A:
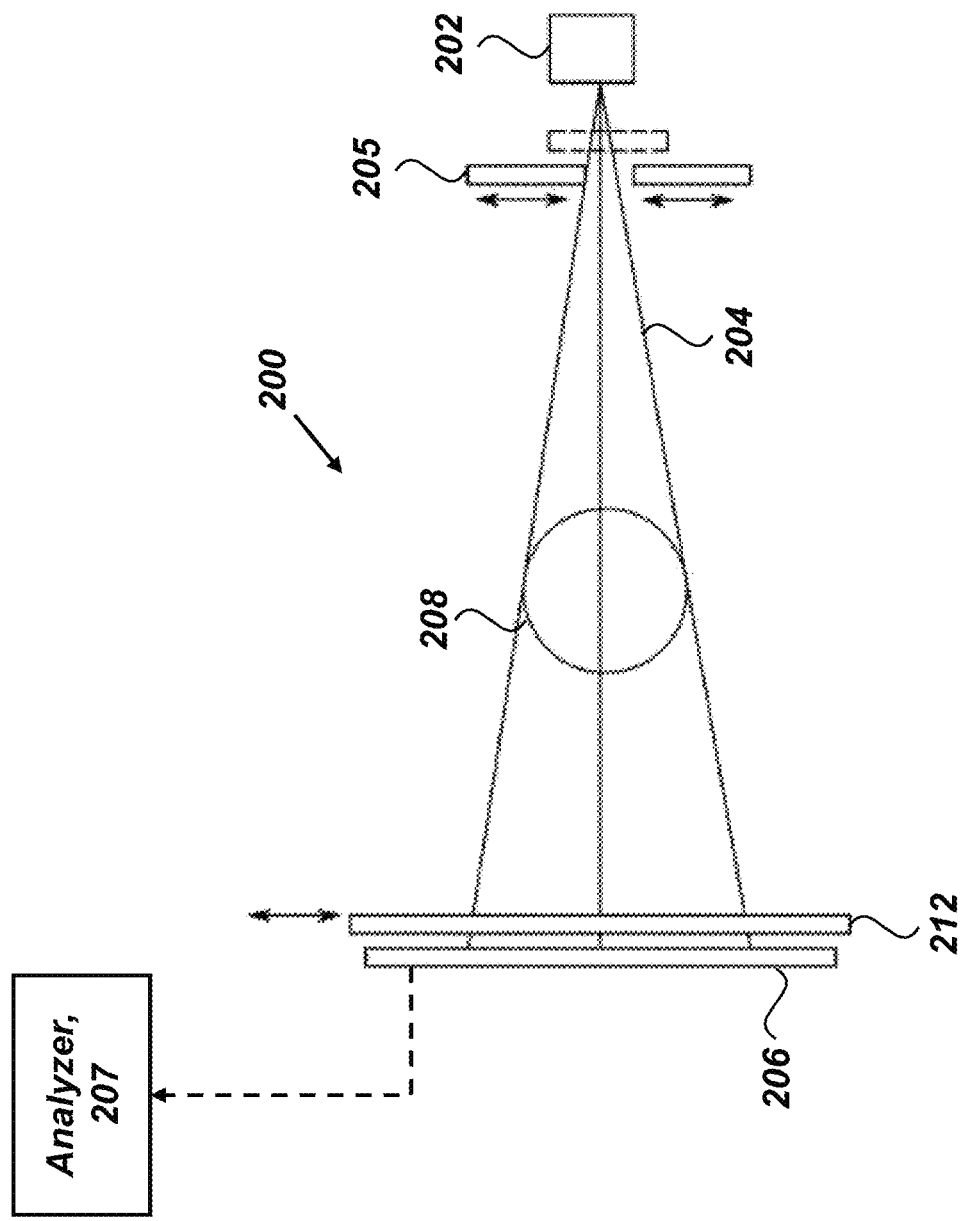
FIG. 1A is a schematic diagram illustrating a top view of one exemplary embodiment of an CT imaging system.

It is noted that the drawings are not necessarily to scale. The drawings are intended to depict only typical aspects of the subject matter disclosed herein, and therefore should not be considered as limiting the scope of the disclosure.

DETAILED DESCRIPTION

When performing x-ray inspection, x-rays can be passed through a target object and detected by a detector to generate images. Some x-rays can be scattered from their initial trajectory, which introduces artifacts that reduce contrast in the images. Techniques for scatter correction have been developed but each have problems. In one example, simulations have been developed to model scatter. However, such simulations can be based upon limited to no experimental data (pure simulation) and/or can rely heavily on interpolation (limited experimental data supplemented by interpolation). Furthermore, not all aspects of scatter can be simulated or interpolated with sufficient exactness. The missing exactness can result in introduction of artifacts in scatter-corrected images. Thus, scatter estimates resulting from these simulations can deviate significantly from actual scatter. Accordingly, improved systems and methods for scatter correction for x-ray inspection (e.g., computed tomography) are provided. Scatter-free images and scattered images can be used as inputs for computational techniques, such as deep learning (e.g., neural networks) or deconvolution models. The scatter-free images can be generated from multiple partial-scatter free images acquired using an aperture plate containing apertures. Each partial scatter-free image is acquired with the aperture plate at a different position and blocks a portion of the scattered x-rays. Sufficient partial scatter-free images can be acquired so that the combination of aperture positions of the aperture plate at the different positions cover an entire scatter image. The combination of partial scatter-free images gives the scatter-free image. Scatter-free images generated in this manner are measured in small collimated areas, without interpolation, resulting in high precision for scatter estimation.

Embodiments of the present disclosure are generally directed to scatter correction for computed tomography (CT) imaging that achieve improved image quality. Such imaging techniques may be useful in a variety of imaging contexts, such as medical imaging, industrial metrology and inspection, security screening, baggage or package inspection, and so forth. Moreover, such imaging techniques may be employed in a variety of imaging systems, such as CT systems, tomosynthesis systems, X-ray imaging systems, and so forth. Though the present discussion provides examples in an industrial inspection context with respect to CT systems resulting in improved measurement and inspection accuracy, one of ordinary skill in the art will readily apprehend that the application of these techniques in other contexts and in other systems is well within the scope of the present techniques.

Figure 1B:
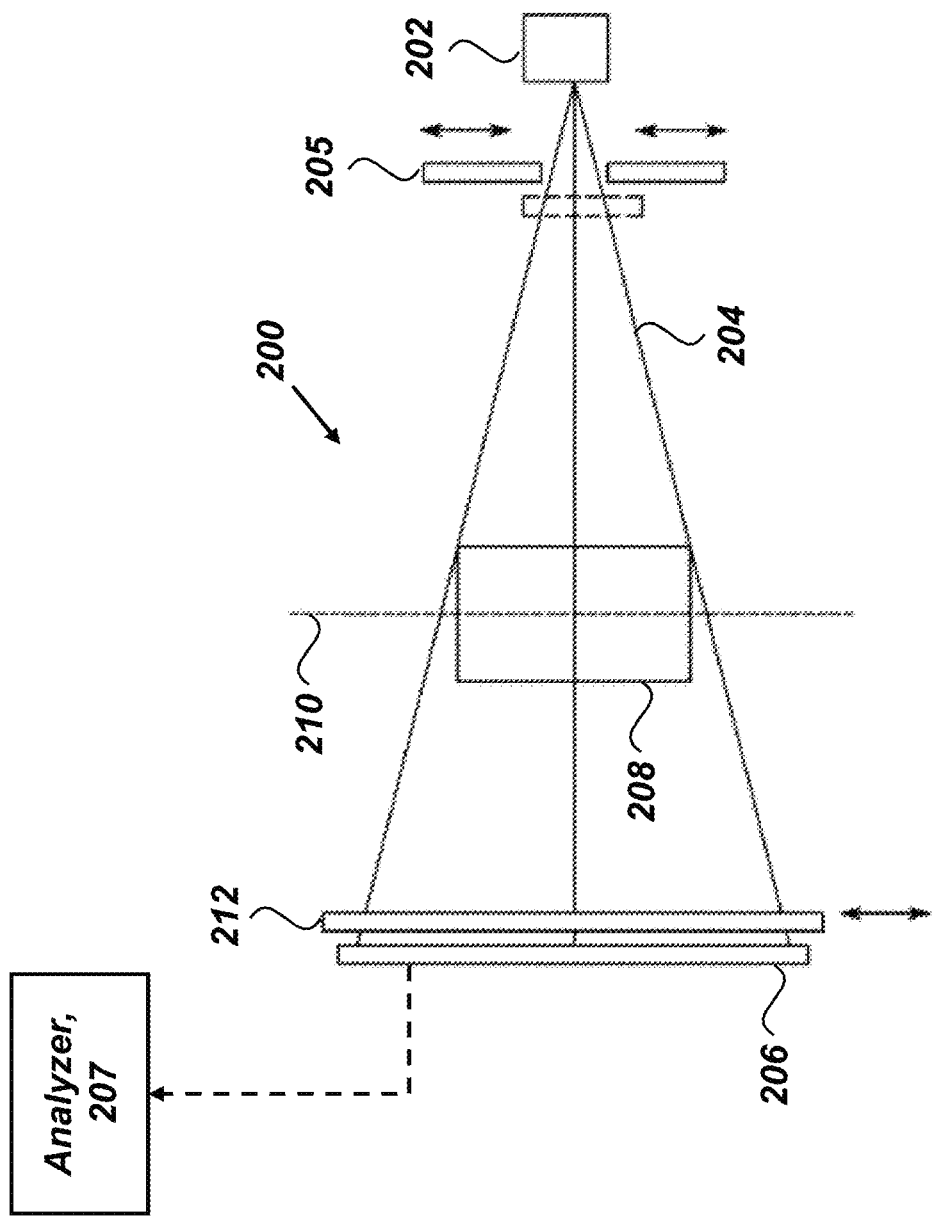
FIG. 1B is a schematic diagram illustrating a side view of the CT imaging system of FIG. 1A.

FIGS. 1A-1B illustrate an imaging system 200 configured to produce a high resolution images. The imaging system 200 can be a volumetric computed tomography (VCT) system designed both to acquire image data and to process the image data for display and analysis. As shown, the imaging system 200 can include a radiation source 202, such as an X-ray source 202. A collimator 205 can be positioned adjacent to the radiation source 202 for collimating the radiation 204 emitted by the radiation source 202 and regulating the size and shape of the emitted radiation 204 emitted by the radiation source 202.

The stream of radiation 204 can be projected toward a detector array 206 placed on the opposite side of the radiation source 202, relative to an object 208 that is to be imaged. The object 208 can be any object suitable for x-ray inspection (e.g., turbine blades). The stream of radiation 204 can pass into an imaging volume in which the object 208 to be imaged. A portion of the radiation 204 passes through or around the object 208 and impacts the detector array 206. The detector array 206 can be generally formed as a two-dimensional array of detection elements. Data collected by the detector array 206 can be output to an analyzer 207 including one or more processors.

The object 208, radiation source 202, and detector array 206 can be displaced relative to each other, allowing projection data to be acquired at various views relative to the object 208 if desired. As an example, the object 208 can be positioned on a table, such as a turntable, so that the object 208 may be rotated about a rotation axis 210. In certain embodiments, data collected from the detector array 206 can undergo pre-processing (e.g., by the analyzer 207) to condition the data to represent the line integrals of the attenuation coefficients of the scanned object 208. The processed data or projections can then be reconstructed (e.g., by the analyzer 207 or another computing device to formulate a volumetric image of the scanned area, as discussed in greater in U.S. Pat. No. 9,804,106, the entirety of which is incorporated by reference.

The imaging system 200 can employ a variety of scatter mitigation and/or correction techniques for improving the image quality and resolution. For example, a scatter rejecting aperture plate 212 for rejecting the scatter radiation resulting from the object 208, as well as those resulting from the background, can be employed. In order to further improve the resolution and image quality, the aperture plate 212 can be movable between a plurality of positions, discussed in greater detail below. By moving the aperture plate 212 between the plurality of positions, smaller structures on the object 208 can be recognized and artifacts can be better avoided.

As discussed in greater detail in U.S. Pat. No. 9,804,106, the aperture plate 212 can include a plurality of sub-centimeter sized apertures 48, such as circular apertures, drilled in a plate. The apertures 48 can be positioned on a two-dimensional grid. Embodiments of the apertures 48 have any geometric shape, such as a circular shape, rectangular shape, or hexagonal shape, among others. In certain embodiments, the circular apertures 48 may be about 1-2 millimeters in diameter spaced apart at about 5 millimeters from each other (center-to-center).

Figure 2B:
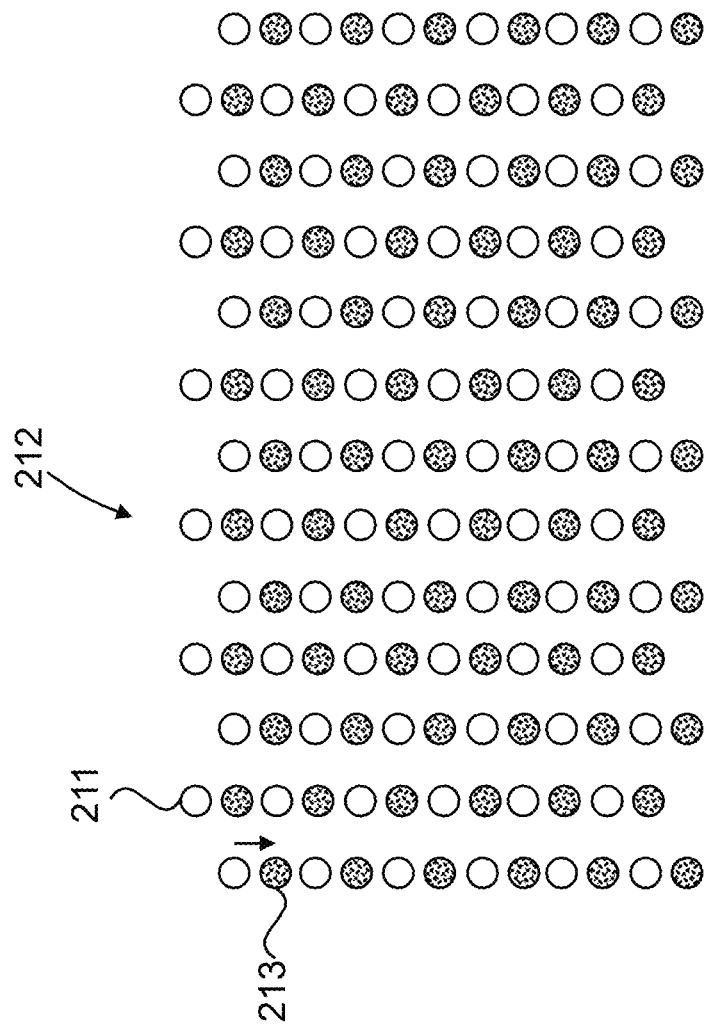
FIG. 2B is a schematic diagram illustrating positions of the apertures of the aperture plate when the aperture plate is located at the first position and a second position that is vertically translated with respect to the first position.
Figure 2C:
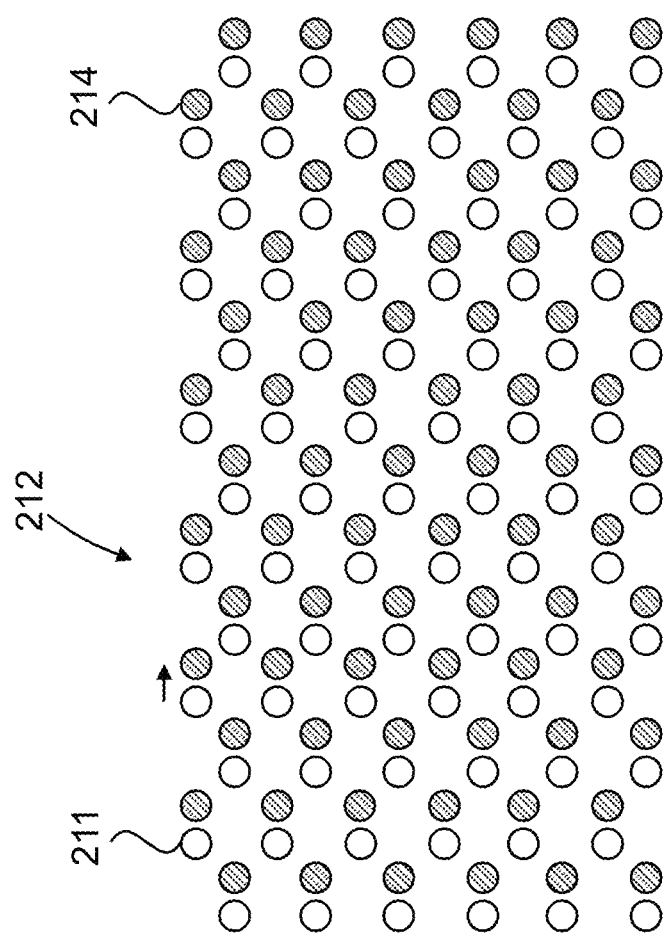
FIG. 2C is a schematic diagram illustrating positions of the apertures of the aperture plate when the aperture plate is located at the first position and a third position that is horizontally translated from the first position.
Figure 2D:
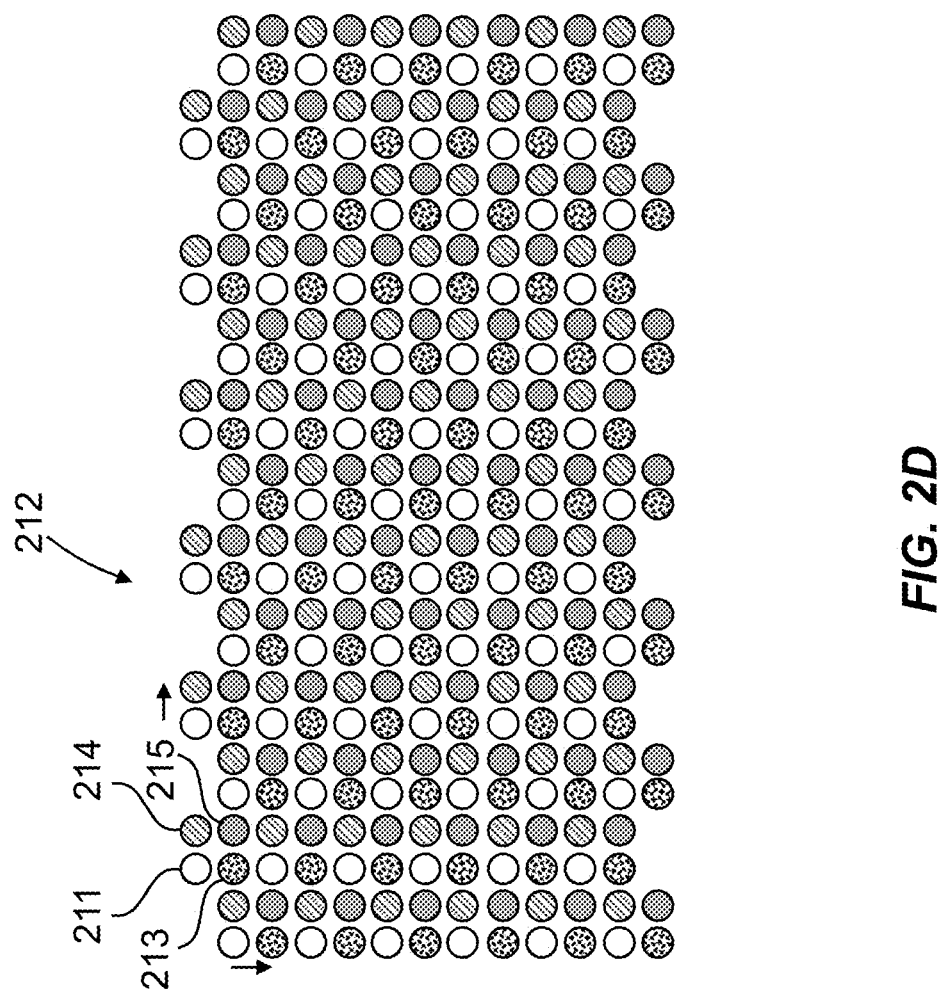
FIG. 2D is a schematic diagram illustrating positions of the apertures of the aperture plate when the aperture plate is located at the first position, the second position, and the third position.
Figure 2E:
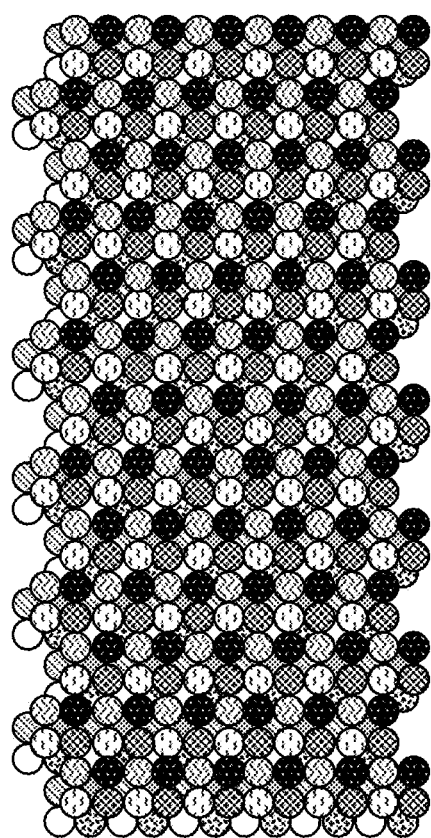
FIG. 2E is a schematic diagram illustrating positions of the apertures of the aperture plate when the aperture plate is located at a plurality of positions that cover substantially all of a desired field of view.

As discussed above, the aperture plate 212 can be movable between a plurality of positions in order to increase the resolution and quality of the generated image. As shown in FIG. 2A, the aperture plate 212 can initially be placed in a first position 211. After a first grid image is gathered, the aperture plate 212 can be repositioned to a secondary position 213, 214 and a second grid image gathered. In an embodiment, the aperture plate 212 can be moved uni-directionally. For example, the aperture plate 212 can be moved vertically from the first position 211 to the second position 213, as illustrated in FIG. 2B, and a second image gathered or the aperture plate 212 can be moved horizontally from the first position 211 to the third position 214, as illustrated in FIG. 2C, and the second image gathered. In another embodiment, the aperture plate 212 can be moved bi-directionally. For example, the aperture plate 212 can be moved both vertically and horizontally, as illustrated in FIG. 2D. In this embodiment, the aperture plate 212 can be placed in a first position 211 and a first image gathered, moved to a second position 213 and a second image gathered, moved to a third position 214 and a third image gathered, and moved to a fourth position 215 and a fourth image gathered. In another embodiment, the aperture plate 212 can be rotated relative to the object 208. An image can be gathered at each position 211, 213, 214, 215 of the aperture plate 212. As shown in FIG. 2E, the process of moving the aperture plate 212 an acquiring an image can be repeated until the aperture positions cover an entire desired area.

In another embodiment, resolution of the image can also be increased by moving the object 208 in front of the grid of the aperture plate 212. Similar to repositioning the aperture plate 212, discussed above, in this embodiment the sample can be moved uni-directionally, bi-directionally, or rotated, for example. By repositioning the apertures 48 of the aperture plate 212 relative to the object 208, the resolution of the image can be increased. The aperture plate 212 and/or object 208 can be repositioned manually or automatically.

The resolution of the image can be determined by the number of positions at which the aperture plate 212 and/or object 208 can be placed. As the number of positions increases, the resolution of the image also increases. For example, using bi-directional movement of the aperture plate 212, positioning the aperture plate 212 in four positions increases the image resolution by a factor of two (2). In another example, positioning the aperture plate 212 in sixteen positions increases the image resolution by a factor of four (4). This improvement in image resolution by repositioning the aperture plate 212 is illustrated by FIGS. 3A-3B.

Figure 3A:
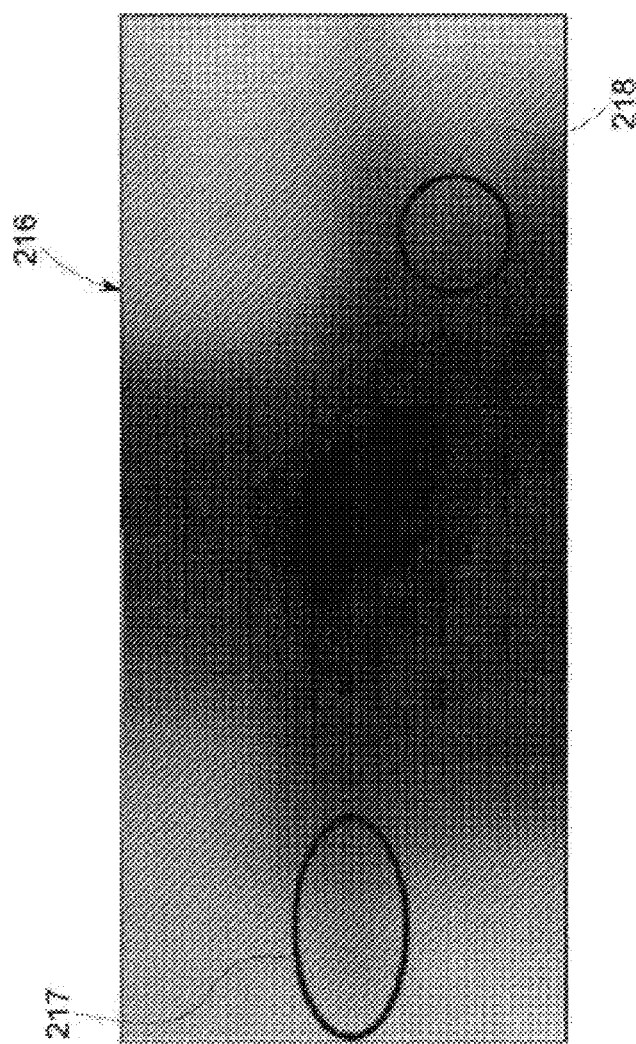
FIG. 3A is a CT image that is scatter corrected using a single position of the aperture plate.
Figure 3B:
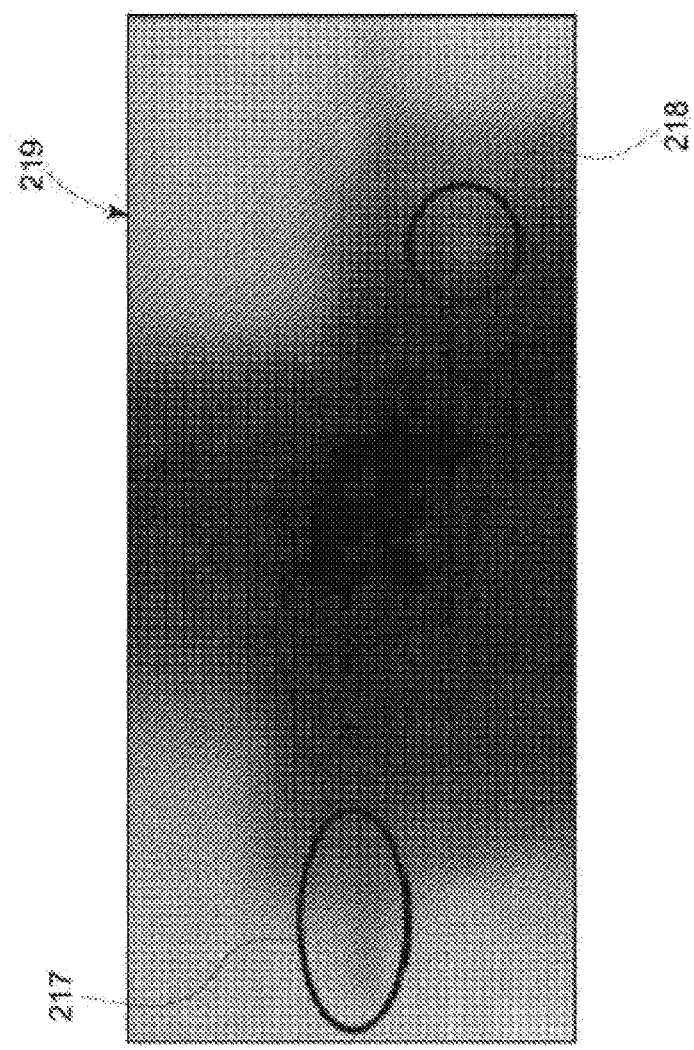
FIG. 3B is a CT image that is scatter corrected using four positions of the aperture plate.

FIG. 3A illustrates an image 216 of the object 208 generated in which the aperture plate 212 was placed in a single position. FIG. 3B illustrates an image 219 of the object 208 in which the aperture plate 212 was placed in four positions during gathering of the data. As illustrated by the first 217 and second 218 location indicated in these figures, the additional positions of the aperture plate 212 results in an image in FIG. 3B in which additional details are visible at each of the first location 217 and the second location 218 as compared to FIG. 3A.

The scatter free image can be used in combination with computational approaches for scatter correction. This combination can create better results and less scanning effort for scatter correction in x-ray tomography. Examples of computational approaches can include deep learning (e.g., neural networks) or deconvolutional approaches.

Figure 4:
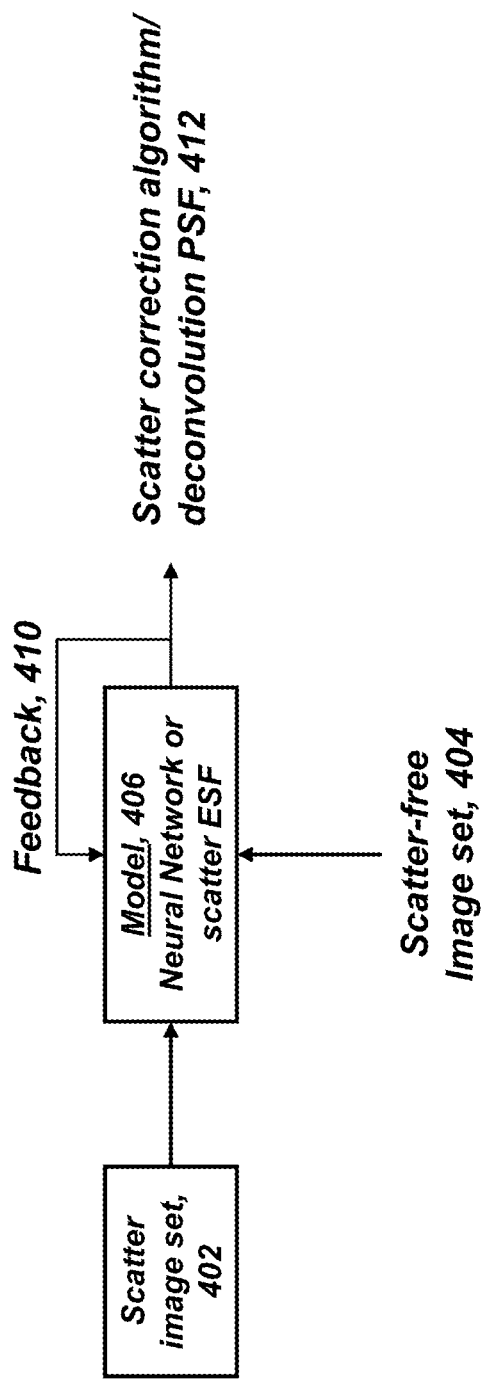
FIG. 4 is a schematic block diagram illustrating computational techniques employing the scatter images and scatter-free images as inputs for development of scatter correction algorithms or deconvolution.

As illustrated in FIG. 4, a set of scatter images 402 and a set of scatter-free images can be input into a model 406 (e.g., a neural network or scatter edge spread function (ESF)). In the case of a neural network, one or more algorithms can be received or generated for scatter correction and applied to the scatter image set 402. In the case of deconvolution, with scatter ESF, a point spread function (PSF) for deconvolution can be received or generated and applied to the scatter image set 402. In either case, deviations between the scatter corrected image set and the scatter-free image set 404 are determined and used as feedback 410 for revision of the algorithms. This process repeats itself, updating the algorithms or parameters each iteration until deviations between the scatter corrected image set and the scatter-free image set 404 are less than a predetermined deviation. Subsequently, the determined algorithm or PSF is output.

Figure 5:
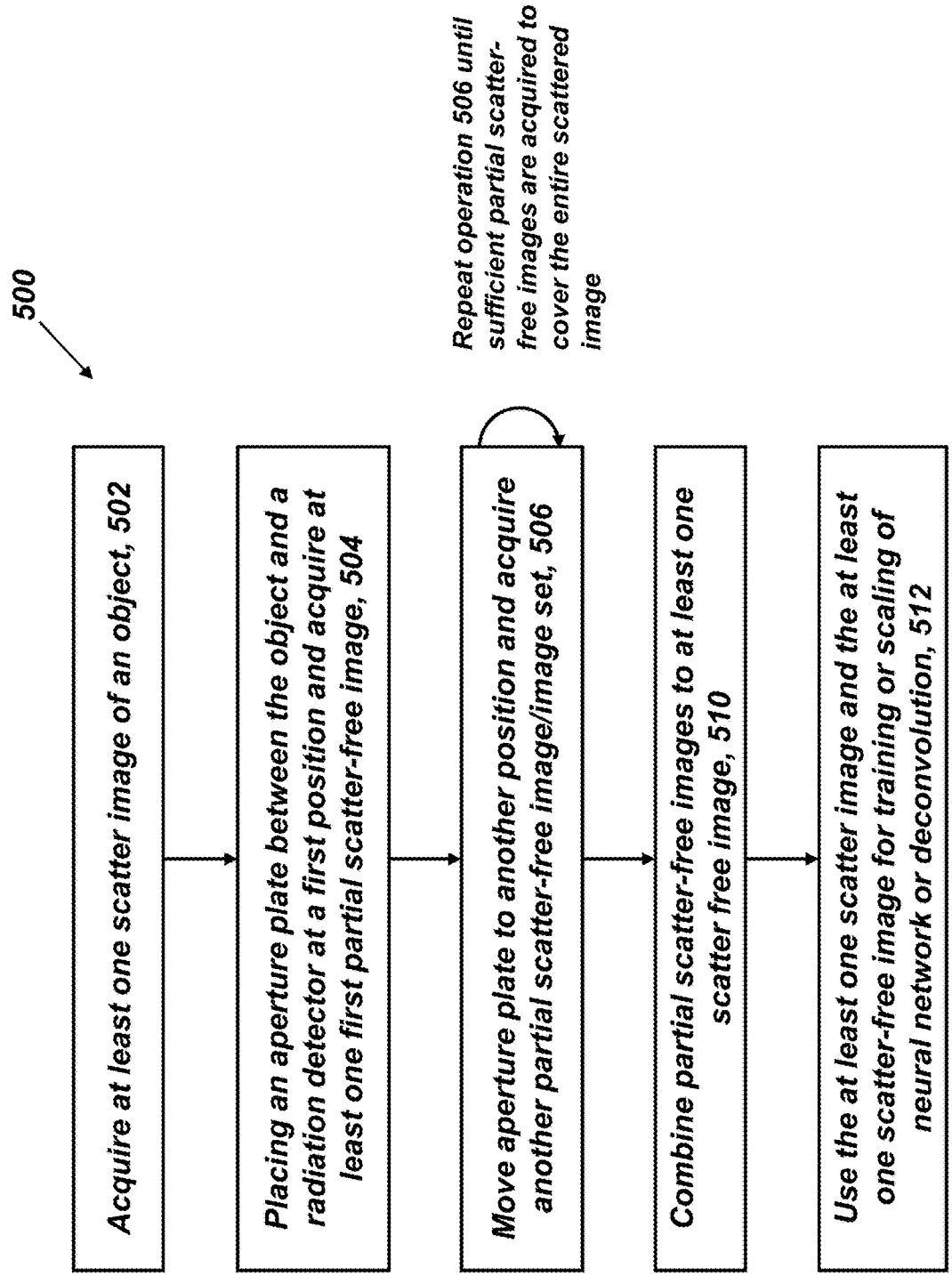
FIG. 5 is a flow diagram illustrating one exemplary embodiment of a method for scatter correction of CT images.

FIG. 5 is a flow diagram illustrating one exemplary embodiment of a method 500 for scatter correction of an image of an object, such as the object 208, by employing an advanced scatter measurement and correction technique on the imaging system 200 is depicted. As shown, the method 500 includes operations 502-512. It can be understood that this method is exemplary only and that selected operations can be altered, added, removed, and/or rearranged as necessary.

In operation 502, at least one scatter image of the object 208 can be acquired. In certain embodiments, a plurality of scatter images (e.g., a scatter image set) can be acquired.

In operation 504, the aperture plate 212 is placed between the object 208 and the detector 206 at a first position. As discussed above, the aperture plate 212 can include the plurality of apertures 211 and can be configured to inhibit scatter radiation (e.g., x-rays scattered from the object 208 and/or background) from detection by the detector array 206. At least one first partial scatter-free image (e.g., a single partial scatter free image or a partial scatter free image set including a plurality of partial scatter free images) can be acquired when the aperture plate 212 is in the first position.

In operation 506, the aperture plate 212 can be moved to one or more other positions (e.g., one or more second positions), different from the first position. As an example, movement of the aperture plate 212 can include translation alone, rotation alone, or combinations of translation and rotation. Translation can include movement in at least one direction (e.g., a horizontal direction, a vertical direction, or combinations thereof). The apertures can overlap or be spaced apart by a predetermined distance between the first and second positions. A second partial scatter-free image or partial scatter-free image set can be acquired when the aperture plate 212 is positioned at selected ones of the second positions (e.g., at least a portion and up to all of the second positions). Operation 506 can be repeated to generate as many partial scatter-free images/image sets as are necessary such that the apertures cover approximately the entire scatter image.

In operation 510, the acquired partial scatter-free images can be received by an analyzer and combined to generate a scatter free image/image set. In certain embodiments, at least a portion of the partial scatter-free images are employed.

In operation 512, the scatter image/image set and the scatter-free image/image set are employed for training of deep learning algorithms or PSF estimation of deconvolution algorithms.

It can be appreciated that changes in an x-ray inspection system can change the images acquired by the x-ray inspection system. Such changes can include, but are not limited to, the x-ray detector, the x-ray source, the target being inspected, and the environment. X-ray detector changes can include one or more of replacement of one x-ray detector with another and changes in detection capability due to aging. X-ray source changes can include any change in the x-ray spectra emitted by the x-ray source. Such changes can occur due to replacement of components of the x-ray source (e.g., filters, tubes, etc.) or replacement of the entire x-ray source with another x-ray source. Changes in the environment can include any changes in x-ray scattering behavior due to the environment surrounding the x-ray source.

As a result of these changes, neural network algorithms that have been trained prior to such changes can introduce errors in output scatter-corrected images. Similarly, deconvolution PSF estimates determined prior to such changes can introduce errors in output scatter-corrected images.

Accordingly, to address the effects of changes in the x-ray inspection system, previously determined neural network algorithms can be retrained or the deconvolution PSF estimates can be updated. That is, the neural network training or deconvolution PSF estimates do not need to be completely regenerated. Beneficially retraining the previously determined neural network algorithm or updating the previously determined PSF estimates can require significantly less training data and time than generation from scratch.

As discussed in greater detail below, retraining a neural network algorithm or updating deconvolution PSF estimates can be performed in a variety of ways. A single image or a whole image set can be employed. The adjustment can valid for one data set and on sample type or for many data sets also with different sample types. The choice of training data depends on the neural network or evaluated PSF, if they was created for general correction or for more specialized cases.

Figure 6:
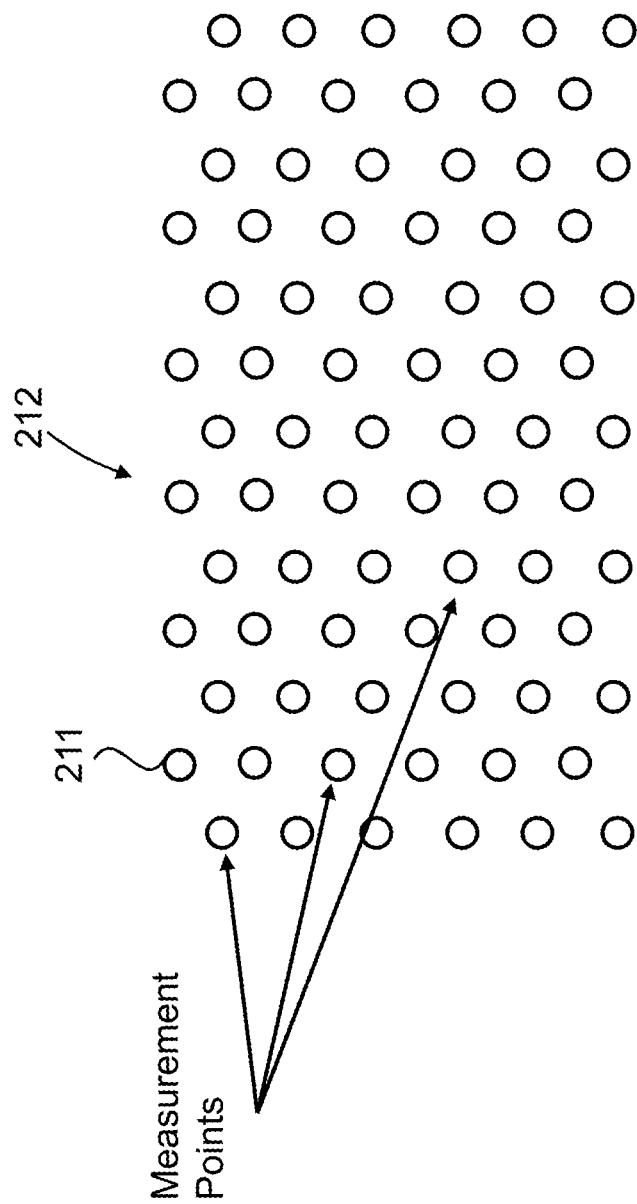
FIG. 6 is a schematic diagram illustrating the high number of measurement points for adjustment, which is given with aperture plate.

FIG. 6 is a schematic illustration of the aperture plate 212 illustrating the high number of different possible measurement points that can be used for acquiring partial scatter-free images for retraining a neural network or adjusting PSF estimates for a deconvolution algorithm.

Figure 7:
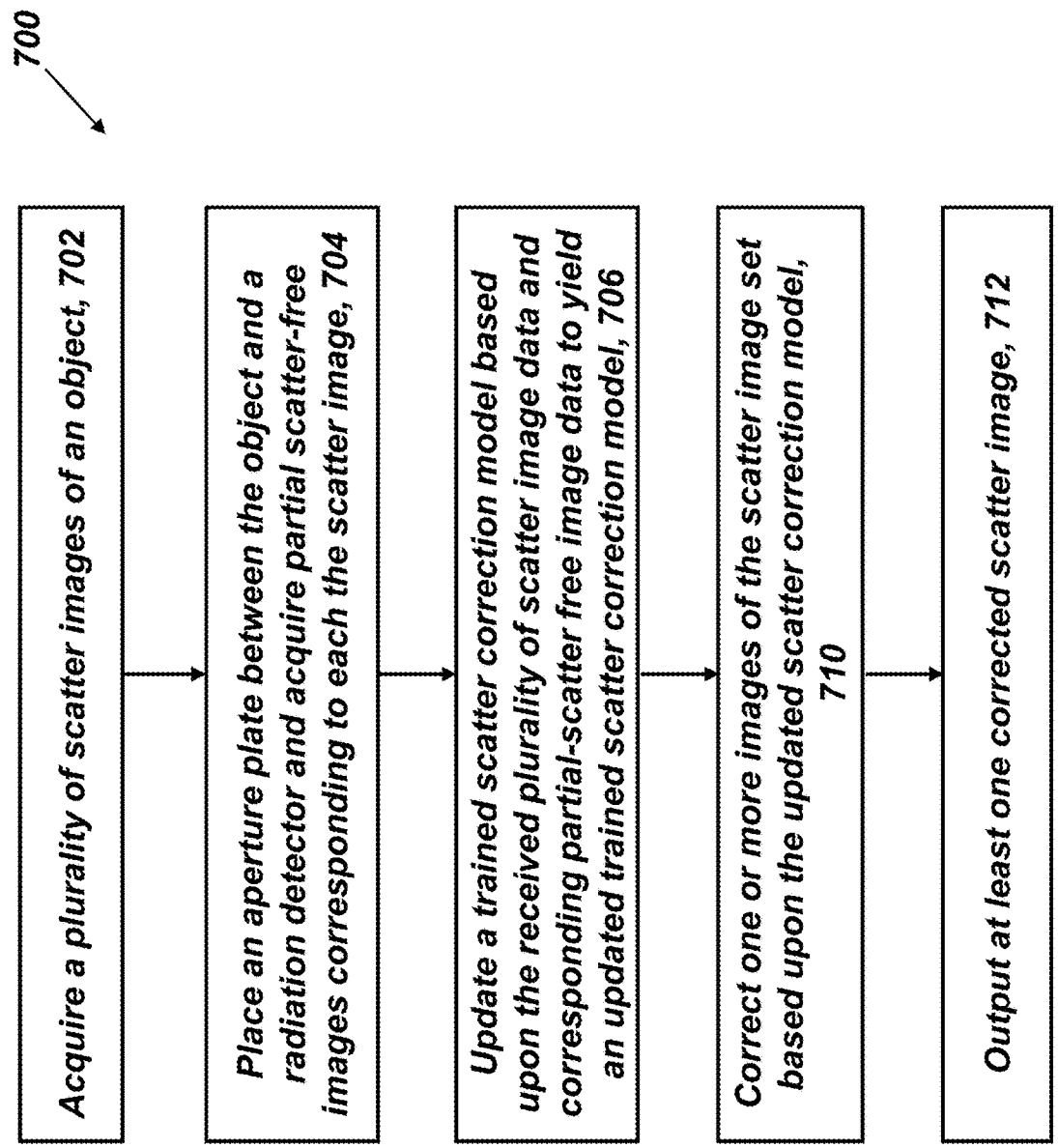
FIG. 7 is a flow diagram illustrating one exemplary embodiment of a method for scatter correction in which a previously trained neural network or previously determined deconvolution PSF is adjusted based upon corresponding pairs of images of a scatter image set and a partial scatter-free image set.

FIG. 7 is a flow diagram of one exemplary embodiment of a method 700 for retraining a neural network or adjusting PSF estimates for a deconvolution algorithm. As shown, the method 700 includes operations 702-712. It can be understood that this method is exemplary only and that selected operations can be altered, added, removed, and/or rearranged as necessary.

In operation 702, a plurality of scatter images (e.g., a set of scatter images) of the object 208 can be acquired.

In operation 704, the aperture plate 212 is placed between the object 208 and the detector 206 and a partial scatter-free image corresponding to each of the acquired scatter images can be acquired by the radiation detector 206. That is, a partial scatter-free image corresponding to a scatter image can be acquired under the same conditions, or approximately the same conditions (e.g., within equipment tolerances) as that scatter image, except that the difference being the presence of the aperture plate 212 during acquisition of the partial scatter-free image.

The acquired scatter image data and partial-scatter free image data can be further received by the analyzer 207. In certain embodiments, the analyzer 207 can receive the acquired scatter image data and partial-scatter free image data directly from the radiation detector 206. In other embodiment, the analyzer 207 can receive the acquired scatter image data and partial-scatter free image data from another source (e.g., a memory device).

In operation 706, the scatter image set and partial scatter-free image set can be employed by the analyzer 207 to retrain (adjust or update) a previously trained scatter correction model (e.g., a previously trained scatter correction algorithm of a neural network or previously determined deconvolution PSF estimates). For scatter correction models employing neural networks, the retraining can include performing an interpolation between the output of the neural network as previously trained for a given scatter image and the corresponding acquired partial scatter-free image. Accordingly, there can be an interpolation determined by the analyzer 207 for each corresponding scatter image and partial scatter-free image pair. The respective interpolations can be employed by the neural network to generate the adjusted scatter correction algorithm. For scatter correction models employing deconvolution approaches, the deconvolution function can be parametrized locally with every measurement point (e.g., each corresponding scatter image and partial scatter-free image pair), rather than generally.

In operation 710, the updated scatter correction model (e.g., neural network algorithm or deconvolution PSF estimates) can be used by the analyzer 207 to correct at least one scatter image of the plurality of scatter images.

In operation 712, at least one of the corrected scatter images can be output by the analyzer 207. For example, the at least one corrected scatter image can be output to a memory device for storage and/or a display device for viewing.

Figure 8:
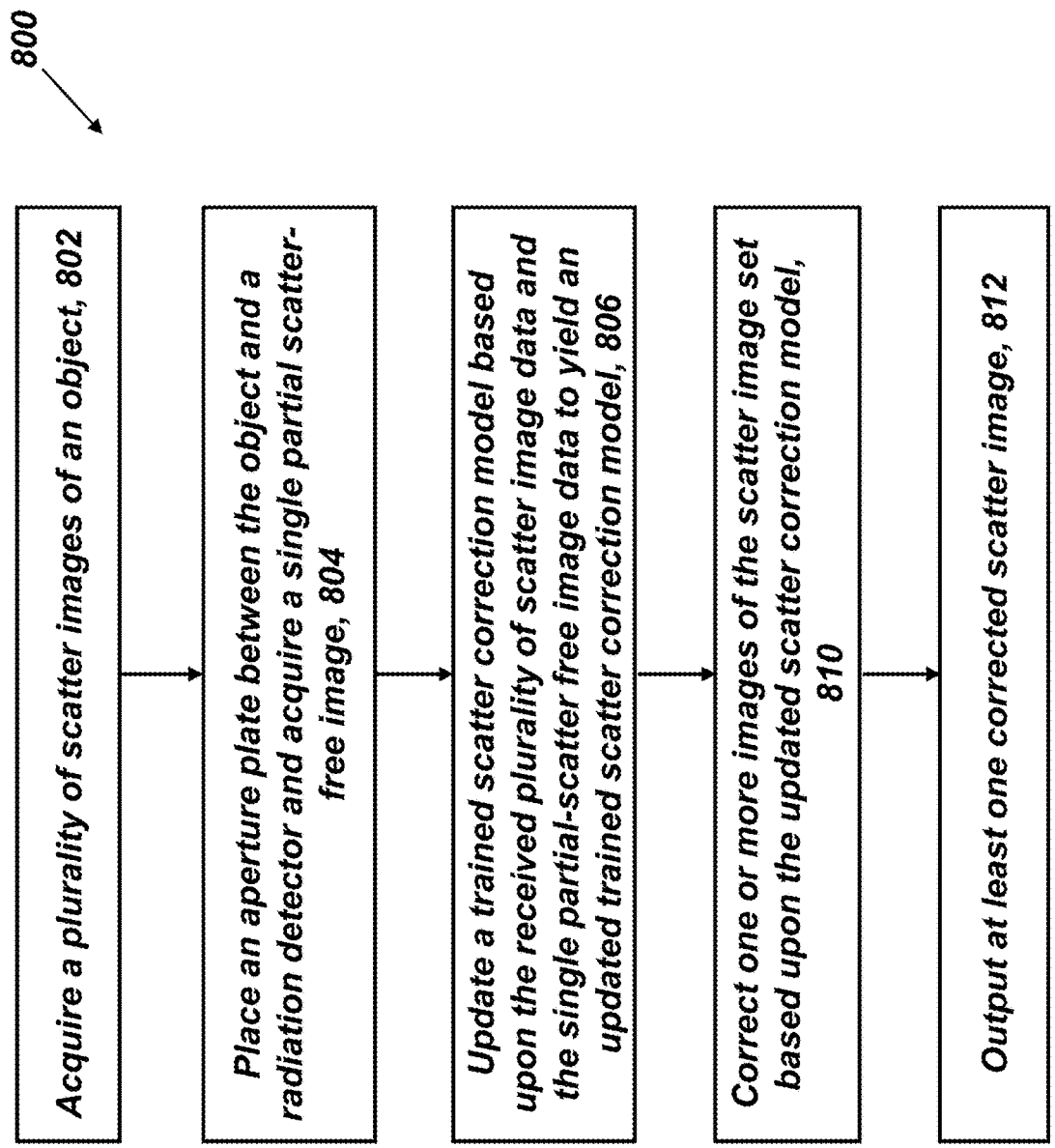
FIG. 8 is a flow diagram illustrating one exemplary embodiment of another method for scatter correction in which a previously trained neural network or previously determined deconvolution PSF is adjusted based upon corresponding pairs of images of a scatter image set and a single partial scatter-free image.

FIG. 8 is a flow diagram of one exemplary embodiment of another method 800 that can be performed by the analyzer 207 for retraining (adjusting or updating) a neural network or PSF estimates for a deconvolution algorithm. As shown, the method 800 includes operations 802-812. It can be understood that this method is exemplary only and that selected operations can be altered, added, removed, and/or rearranged as necessary.

In operation 802, a plurality of scatter images (e.g., a set of scatter images) of the object 208 can be acquired by the radiation detector 206.

In operation 804, the aperture plate 212 is placed between the object 208 and the detector 206 and a single partial scatter-free image can be acquired by the radiation detector 206.

The acquired scatter image data and partial-scatter free image data can be further received by the analyzer 207. In certain embodiments, the analyzer 207 can receive the acquired scatter image data and partial-scatter free image data directly from the radiation detector 206. In other embodiment, the analyzer 207 can receive the acquired scatter image data and partial-scatter free image data from another source (e.g., a memory device).

In operation 806, the plurality of scatter image data and the single partial scatter-free image data can be employed to retrain (e.g., adjust or update) a previously trained scatter correction model (e.g., a previously trained scatter correction algorithm of a neural network or previously determined deconvolution PSF estimates). For scatter correction models employing neural networks, the retraining can include performing an interpolation between the output of the neural network as previously trained for a given scatter image and the single acquired partial scatter-free image. Accordingly, there can be an interpolation determined by the analyzer 207 for each scatter image and single partial scatter-free image pair. The respective interpolations can be employed by the neural network to generate the adjusted scatter correction algorithm. For scatter correction models employing deconvolution approaches, the deconvolution function can be parametrized locally with every measurement point (e.g., each scatter image and single partial scatter-free image pair), rather than generally.

In operation 810, the updated scatter correction model (e.g., neural network algorithm or deconvolution PSF estimates) can be used by the analyzer 207 to correct at least one scatter image of the plurality of scatter images.

In operation 812, at least one of the corrected scatter images can be output by the analyzer 207. For example, the at least one corrected scatter image can be output to a memory device for storage and/or a display device for viewing.

Figure 10A:
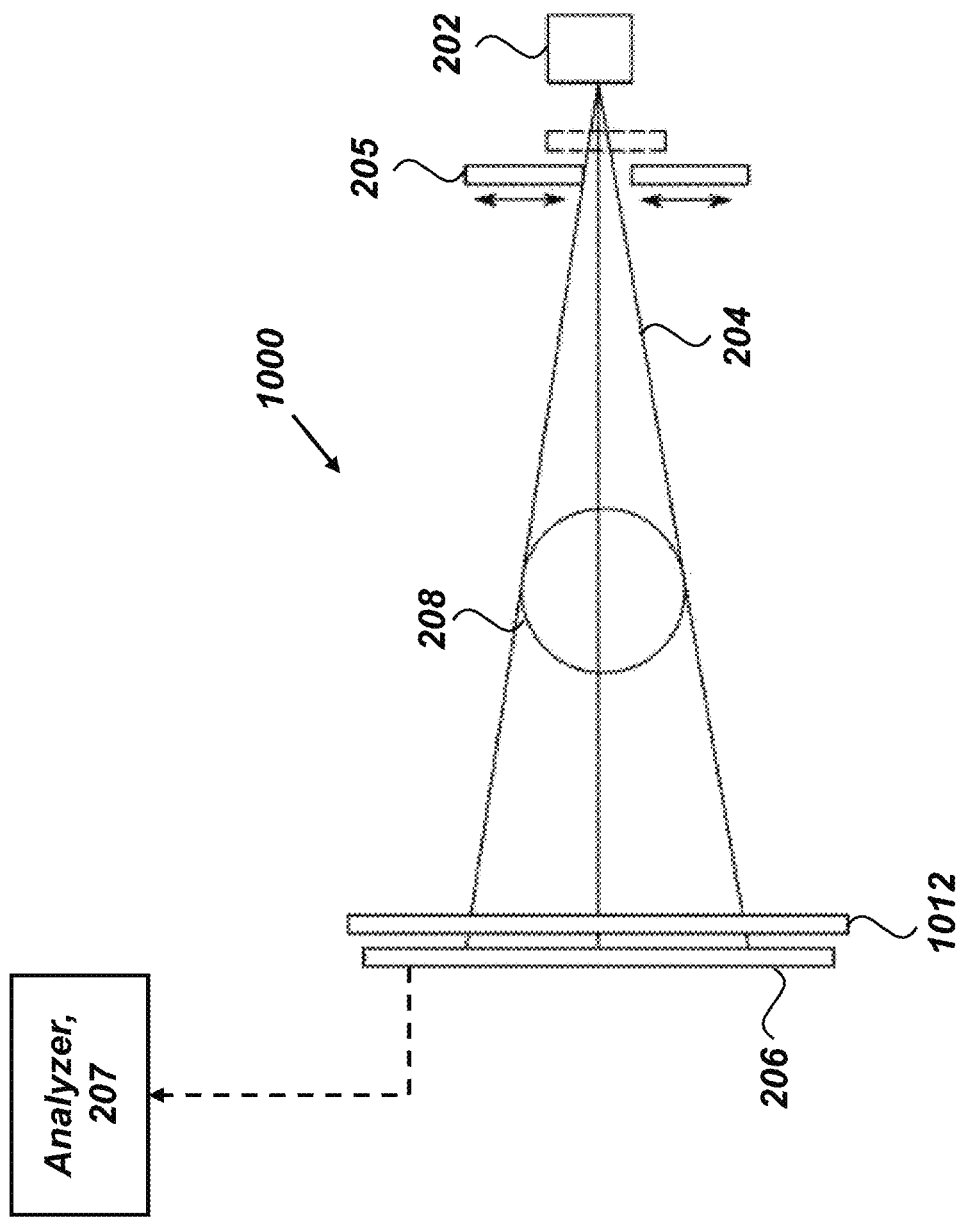
FIG. 10A is a schematic diagram illustrating a top view of one exemplary embodiment of an CT imaging system.
Figure 10B:
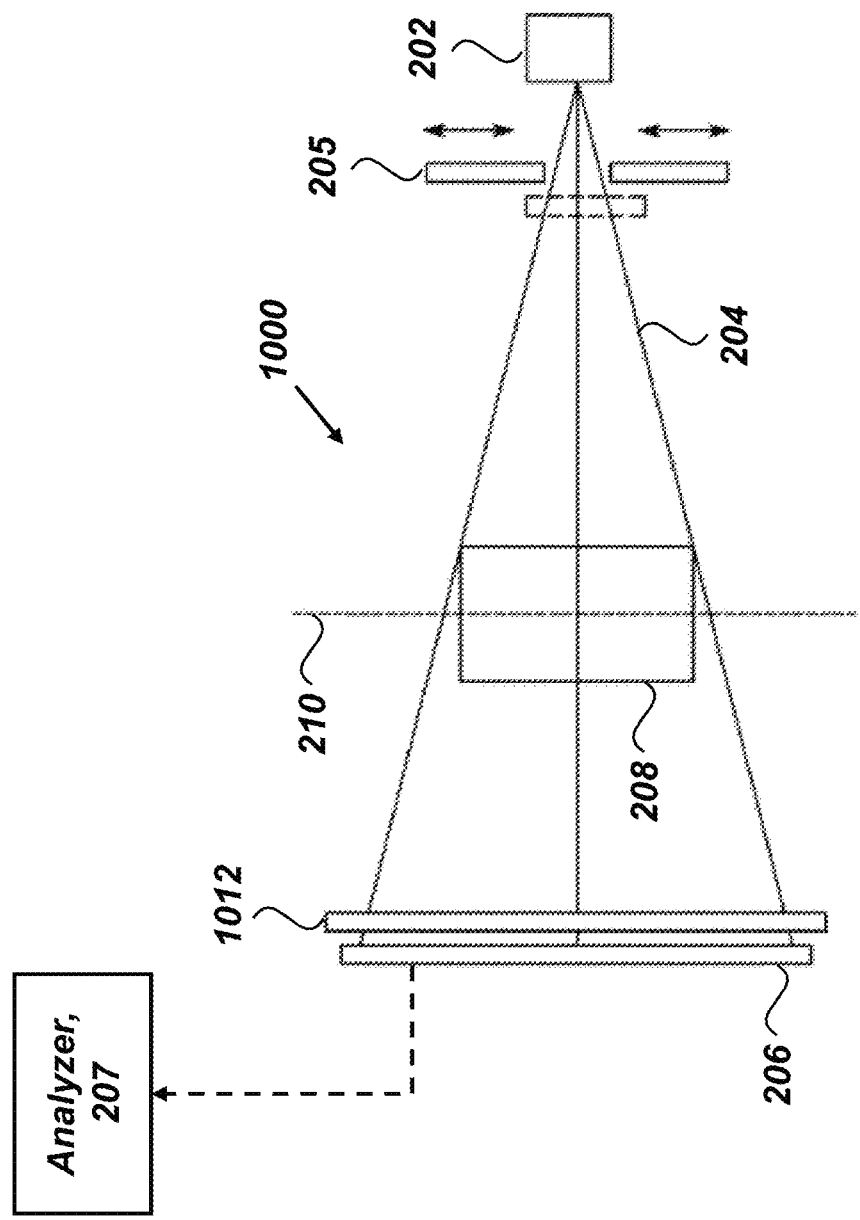
FIG. 10B is a schematic diagram illustrating a side view of the CT imaging system of FIG. 10A.

Under circumstances where a single partial scatter-free image is acquired for adjustment, the x-ray inspection system can optionally omit the capability of moving the aperture plate 212, as illustrated in FIGS. 10A-10B.

The choice of whether to employ the method 700 or method 800 for adjusting the neural network or deconvolution ESF can depend upon the use case and needed accuracy of scatter correction. As an example, under circumstances where each inspected object 208 is the same, the single partial-free image approach of method 800 can be sufficient. This measurement can be performed periodically to adjust the neural network or deconvolution ESF to account for aging of components.

Figure 9:
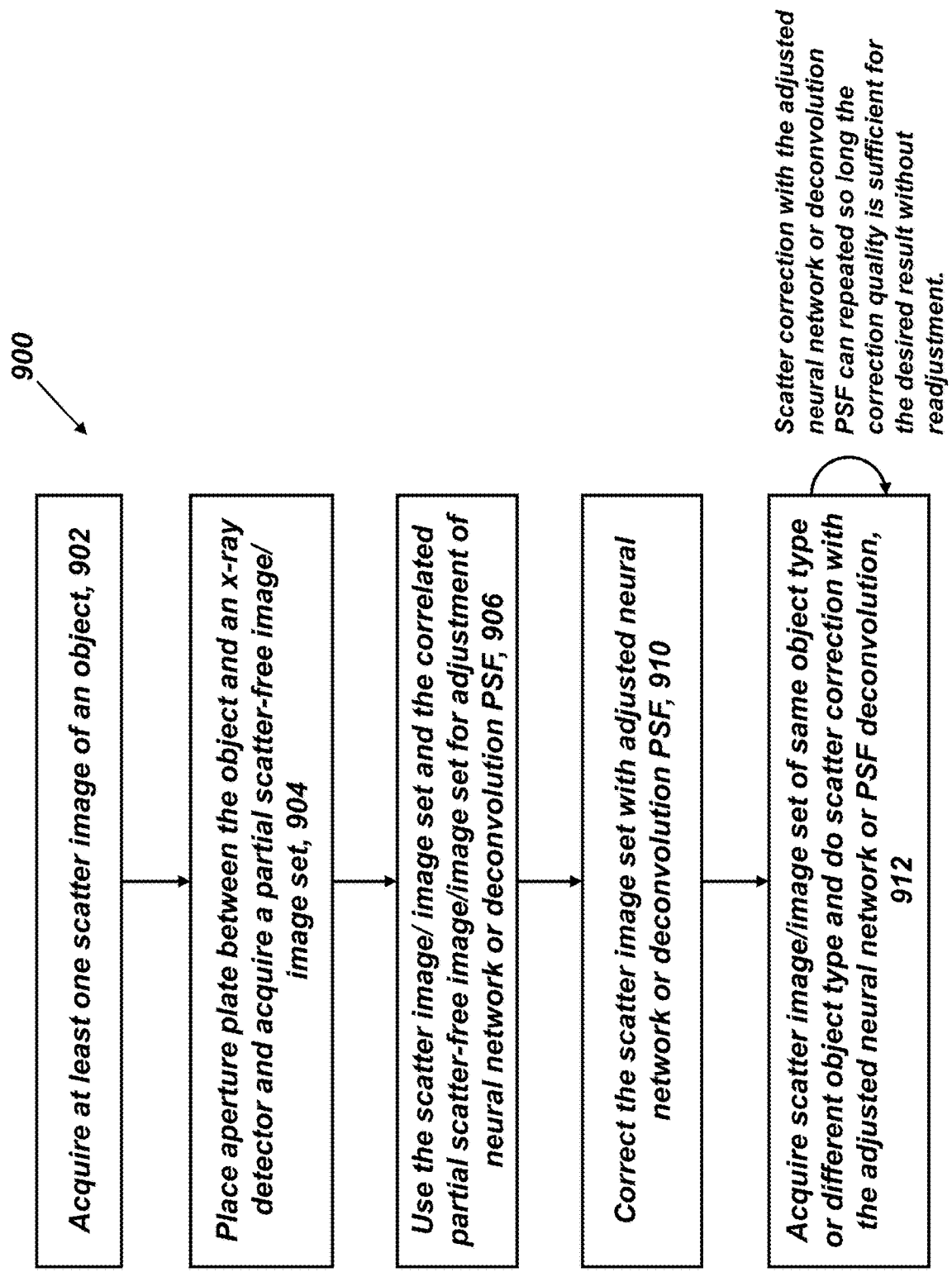
FIG. 9 is a flow diagram illustrating one exemplary embodiment of a further method for scatter correction in which a previously trained neural network or previously determined deconvolution PSF is adjusted based upon an undefined number of scatter image sets for different object types where a single partial-scatter free image or partial scatter-free image set is employed.

FIG. 9 is a flow diagram of one exemplary embodiment of a further method 900 for retraining (adjusting) a neural network or PSF estimates for a deconvolution algorithm. As shown, the method 900 includes operations 902-912. It can be understood that this method is exemplary only and that selected operations can be altered, added, removed, and/or rearranged as necessary.

In operation 902, a scatter image or a set of scatter images of the object 208 are acquired.

In operation 904, the aperture plate 212 is placed between the object 208 and the detector 206 and a single partial scatter-free image or a partial scatter-free image set is acquired. As noted above, when acquiring a set of partial scatter-free images, each image of the scatter free image set can correspond to respective images of the scatter image set.

In operation 906, the scatter image set and the single partial scatter-free image or scatter-free image set can be employed to retrain (adjust) the previously trained neural network or previously determined deconvolution PSF estimates. Adjustment performed using the partial scatter-free image set can be performed as discussed above in operation 706. Adjustment performed using the single partial scatter-free image can be performed as discussed above in operation 806.

In operation 910, the adjusted neural network algorithm or deconvolution PSF estimates can be used to correct the scatter image set.

In operation 912, a scatter image or scatter image set of the same type of object 208 or different type of object 208 can be acquired. Scatter correction can be performed using the adjusted neural network algorithm or deconvolution PSF estimates. Operation 912 can be repeated so long as the correction quality is sufficient for the desired result without readjustment.

Exemplary technical effects of the methods, systems, and devices described herein include, by way of non-limiting example improved scatter correction for x-ray images. A scatter free image can be generated from a plurality of partial scatter-free images acquired using an aperture plate positioned at different positions. The scatter-free image can used in combination with computational approaches (e.g., deep learning, deconvolution, etc.) for scatter correction. This combination can create better results and less scanning effort for scatter correction in x-ray tomography.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data.

Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

The invention claimed is:

1. A method for scatter correction of an image of an object, comprising:
   acquiring, by a radiation detector of an imaging system, data representing a plurality of scatter images of an object based upon detection of radiation that is transmitted through an imaging volume of the object;
   placing an aperture plate between the object and the radiation detector, the aperture plate comprising a plurality of apertures configured to inhibit scattered radiation from detection by the radiation detector;
   acquiring, by the radiation detector, data representing a partial scatter-free image corresponding to each scatter image, wherein each partial scatter-free image is based upon detection of radiation that is transmitted through the imaging volume of the object when the aperture plate is present, and wherein the scatter image and its corresponding partial scatter-free image are acquired under approximately the same conditions except for the presence of the aperture plate;
   receiving, by an analyzer comprising one or more processors, the plurality of scatter image data and corresponding partial-scatter free image data;
   receiving, by the analyzer, a trained scatter correction model, wherein the trained scatter correction model is a trained neural network model;
   updating, by the analyzer, the trained scatter correction model based upon the received plurality of scatter image data and corresponding partial-scatter free image data, to yield an updated trained scatter correction model, wherein the updating comprises
      for each pair of corresponding scatter image and partial scatter-free images, performing an interpolation between the output of the trained neural network model for the scatter image and the output of the trained neural network model for the partial scatter-free image; and
      generating the updated trained scatter correction model based upon the interpolation;
   correct, by the analyzer, at least one of the plurality of scatter images based upon the updated trained scatter correction model; and
   output, by the analyzer, at least one corrected scatter image.

2. The method of claim 1, wherein the trained scatter correction model comprises a previously determined deconvolution point spread function (PSF) estimate.

3. The method of claim 2, wherein updating the trained scatter correction model comprises:

locally parametrizing the deconvolution PSF estimate using measurement points of respective pairs of corresponding scatter image and partial scatter-free images; and updating the deconvolution PSF estimate based upon the local parametrization.

4. An imaging system, comprising:
a radiation source configured to emit radiation directed towards an object;
a radiation detector configured to detect the emitted radiation transmitted through an imaging volume of the object; and
an analyzer including one or more processors and configured to:
receive data representing a plurality of scatter images of an object based upon detection of radiation by the radiation source that is transmitted through an imaging volume of the object;
receive data representing a partial scatter-free image corresponding to each scatter image, wherein each partial scatter-free image is based upon detection of radiation that is transmitted through the imaging volume of the object when the aperture plate is present, and wherein the scatter image and its corresponding partial scatter-free image are acquired under approximately the same conditions except for the presence of the aperture plate;
receive a trained scatter correction model, wherein the trained scatter correction model is a trained neural network model;
update the trained scatter correction model based upon the received plurality of scatter image data and corresponding partial-scatter free image data, to yield an updated trained scatter correction model, wherein the updating comprises
for each pair of corresponding scatter image and partial scatter-free images, performing an interpolation between the output of the trained neural network model for the scatter image and the output of the trained neural network model for the partial scatter-free image; and
generating the updated trained scatter correction model based upon the interpolation;
correct at least one of the plurality of scatter images based upon the updated trained scatter correction model; and
output at least one corrected scatter image.

5. The imaging system of claim 4, wherein the trained scatter correction model comprises a previously determined deconvolution point spread function (PSF) estimate.

6. The imaging system of claim 5, wherein updating the trained scatter correction model comprises:
locally parametrizing the deconvolution PSF estimate using measurement points of respective pairs of corresponding scatter image and partial scatter-free images; and
updating the deconvolution PSF estimate based upon the local parametrization.

7. A method for scatter correction of an image of an object, comprising:
acquiring, by a radiation detector of an imaging system, data representing a plurality of scatter images of an object based upon detection of radiation that is transmitted through an imaging volume of the object;
placing an aperture plate between the object and the radiation detector, the aperture plate comprising a plurality of apertures configured to inhibit scattered radiation from detection by the radiation detector;

acquiring, by the radiation detector, data representing a single partial scatter-free image, wherein the single partial scatter-free image is based upon detection of radiation that is transmitted through the imaging volume of the object when the aperture plate is present;
receiving, by an analyzer comprising one or more processors, the plurality of scatter image data and the single partial-scatter free image data;
receiving, by the analyzer, a trained scatter correction model, wherein the trained scatter correction model is a trained neural network model;
updating, by the analyzer, the trained scatter correction model based upon the received plurality of scatter image data and the single partial-scatter free image data, to yield an updated trained scatter correction model, wherein the updating comprises
for each pair of corresponding scatter image and partial scatter-free images, performing an interpolation between the output of the trained neural network model for the scatter image and the output of the trained neural network model for the partial scatter-free image; and
generating the updated trained scatter correction model based upon the interpolation;
correct, by the analyzer, at least one of the plurality of scatter images based upon the updated trained scatter correction model; and
output, by the analyzer, at least one corrected scatter image.

8. The method of claim 7, wherein the trained scatter correction model comprises a previously determined deconvolution point spread function (PSF) estimate.

9. The method of claim 8, wherein updating the trained scatter correction model comprises:
locally parametrizing the deconvolution PSF estimate using measurement points of respective image pairs comprising a scatter image of the plurality of scatter images and the single partial scatter-free image; and
updating the deconvolution PSF estimate based upon the local parametrization.

10. An imaging system, comprising:
a radiation source configured to emit radiation directed towards an object;
a radiation detector configured to detect the emitted radiation transmitted through an imaging volume of the object; and
an analyzer including one or more processors and configured to:
receive data representing a plurality of scatter images of an object based upon detection of radiation by the radiation source that is transmitted through an imaging volume of the object;
receive data representing a single partial scatter-free image, wherein the single partial scatter-free image is based upon detection of radiation that is transmitted through the imaging volume of the object when the aperture plate is present;
receive a trained scatter correction model, wherein the trained scatter correction model is a trained neural network model;
update the trained scatter correction model based upon the received plurality of scatter image data and the single partial-scatter free image data, to yield an updated trained scatter correction model, wherein the updating comprises
for each pair of corresponding scatter image and partial scatter-free images, performing an interpolation between the output of the trained neural network model for the scatter image and the output of the trained neural network model for the partial scatter-free image; and generating the updated trained scatter correction model based upon the interpolation;

correct at least one of the plurality of scatter images based upon the updated trained scatter correction model; and output at least one corrected scatter image.

11. The imaging system of claim 10, wherein the trained scatter correction model comprises a previously determined deconvolution point spread function (PSF) estimate.

12. The imaging system of claim 11, wherein updating the trained scatter correction model comprises:

locally parametrizing the deconvolution PSF estimate using measurement points of respective image pairs comprising a scatter image of the plurality of scatter images and the single partial scatter-free image; and updating the deconvolution PSF estimate based upon the local parametrization.

* * * * *